United States Patent [19]
Nattermann

[11] Patent Number: 5,294,861
[45] Date of Patent: Mar. 15, 1994

[54] ULTRASONIC PROBE
[75] Inventor: Kurt Nattermann, Ingelheim, Fed. Rep. of Germany
[73] Assignee: Schott Glaswerke, Mainz, Fed. Rep. of Germany
[21] Appl. No.: 830,157
[22] Filed: Feb. 3, 1992
[30] Foreign Application Priority Data
Feb. 2, 1991 [DE] Fed. Rep. of Germany ......... 103145
[51] Int. Cl.$^5$ ............................................. H01L 41/08
[52] U.S. Cl. ................................. 310/334; 310/328; 333/141
[58] Field of Search ................. 310/334, 328; 333/141, 333/147

[56] References Cited
U.S. PATENT DOCUMENTS

| | | | |
|---|---|---|---|
| 3,593,214 | 7/1971 | Cooper | 310/334 |
| 3,605,043 | 9/1971 | Bienrenu et al. | 310/334 |
| 3,719,907 | 3/1973 | Adler | 310/334 |
| 3,757,257 | 9/1973 | Knitter | 310/334 |
| 3,796,974 | 3/1974 | Khanovich et al. | 310/334 |
| 3,975,698 | 8/1976 | Redman | 310/334 |
| 4,016,515 | 4/1977 | Wauk | 310/334 |

OTHER PUBLICATIONS

"Acoustic Waveguides for Sensing and Locating Electrical Discharges in High Voltage Power Transformers and Other Apparatus", by R. Harrold, Mar./Apr. 1979, IEEE Transactions on Power Apparatus and Systems.

Primary Examiner—Steven L. Stephan
Assistant Examiner—Thomas M. Dougherty
Attorney, Agent, or Firm—Millen, White, Zelano & Branigan

[57] ABSTRACT

An ultrasonic probe is disclosed wherein the sonic energy is transmitted by sonic waveguides from ultrasonic transducers at the proximal end of the probe to the ultrasonic directional elements at the distal end. The sonic waveguides are designed so that the sound waves are transmitted in a pure mode fashion and show low transmission losses and low dispersion. The ultrasonic probe is suitable especially for medical endosonography.

22 Claims, 2 Drawing Sheets

ULTRASONIC PROBE

BACKGROUND OF THE INVENTION

The invention relates to an ultrasonic probe.

Ultrasonic probes are utilized, for example, in medical sonography.

So-called ultrasonic pulse echo processes are known wherein ultrasonic pulses are beamed into tissue and the signals reflected by the tissue are recorded, for example in order to draw conclusions regarding the depth structure of the tissue from the time curve of the reflected signals. In the so-called ultrasonic Doppler methods, the shift in the frequency of the reflected signal with respect to the beamed-in signal is measured to determine therefrom, for example, the velocity of the reflecting structure. In most cases, ultrasonic pulses are used having a carrier frequency $f_o$, a pulse duration $T_p$, and a repetition rate $f_w$ (pulses per second).

In order to obtain a high local resolution in these methods, it is necessary to provide a short sound wavelength $\lambda_o$ and/or a high carrier frequency $f_o$ ($\lambda_o = c_o/f_o$; $\lambda_o$: average sound wavelength, $c_o$: average sonic velocity of the medium for the energized wave type). On the other hand, the carrier frequency $f_o$ must not be too high because otherwise the attenuation of the sound waves by absorption or scattering becomes too extensive. For many media, in the relevant frequency ranges, the ultrasonic absorption increases in an approximation with the second power of the frequency and scattering increases even with the fourth power of the frequency. Therefore, in medical sonography, one is generally restricted to the frequency range of a few MHz. However, for examinations wherein only a minor penetration depth is necessary, the frequency can amount under certain circumstances to up to 20 MHz, for example, G. S. Werner et al., "Intravaskuläre Ultraschalldiagnostik" [Intravascular Ultrasonic Diagnostics], Dtsch. med. Wschr. 115: 1259 (1990).

In the pulse echo processes, it is advantageous to utilize pulses of a short duration $T_p$ because, for example, the depth of focus of the probe is also limited by the spatial pulse length $L_p \approx c_o \cdot T_p$. On the other hand, it makes no sense to use pulses having a duration $T_p < 1/f_o$ because in such a case there is no longer any gain in spatial resolution.

The Doppler methods usually require a minor local resolution but, on the other hand, it is important to measure velocities precisely. As a rule of thumb, it can be noted that the measuring accuracy is on a scale of $\Delta c \approx c_o \cdot \Delta f/f_o$ wherein the frequency width $\Delta f$ of the sonic pulses is reciprocal to the pulse duration, $\Delta f \approx 1/T_p$ and $\Delta c \approx c_o/(T_p \cdot f_o)$: thus, high frequencies and long pulses can be advantageous. In the extreme case, continuous-dash signals are even employed with $T_p \gg 1/f_o$; local resolution in this case is only produced by the directional effect of the sonic head.

The sonic head of an ultrasonic probe normally consists of an imaging system, the so-called ultrasonic directional element, and electromechanic ultrasonic transducers directly mounted thereto. In the simplest instance, a sonic head comprises a substantially homogeneous directional element, the typical transverse dimensions of which, characterized by D, are large as compared to the average sonic wavelength in the tissue to be examined: $D > \lambda_o$. In this case, the directional element exhibits a directional characteristic, i.e. the emitted ultrasonic energy is distributed over a narrow zone about its axis, and the element receives essentially only sound emanating from a narrow zone about its axis. If the directional element is, for example, a rotating lobe radiator, then the full aperture angle ("3 dB width") for the "main lobe" amounts, in the arc measure, to $\Delta \theta \approx 0.52 \cdot (\lambda_o/D)$. A description of the rotating lobe radiator is found, for example, in H. Kuttruff, "Physic und Technik des Ultraschalls" [Physcis and Technology of Ultrasound], S. Hirzel publishers, 1988 (ISBN: 3-7776-0427-5). The manner in which the directional characteristic of ultrasonic directional elements, such as the rotating lobe radiator, can be improved is known; this can be done, for example, by the use of focusing elements. In this way, regions for ultrasonic examination can be highlighted along the axis of the directional element (regions of increased ultrasound intensity during beaming and/or reception), in order to be able to investigate these regions, for example, by means of Doppler methods with long pulses.

The examination of spatial structures requires scanning in one or two directions. In the simplest case, a single sonic head is guided, for this purpose, along the surface of the body; the measuring results thereof are combined into a two-dimensional image (path and depth). An overview regarding scanning methods is found in R. Millner (editor), "Ultraschalltechnik-Grundlagen and Anwendungen" [Ultrasonic Technique—Fundamentals and Applications], Physik publishers Weinheim, 1987 (ISBN: 3-87664-106-3).

Percutaneous studies of deep structures have the drawback, inter alia, that the ultrasonic waves are too strongly attenuated at the site of the investigation, whereby local resolution is diminished. Furthermore, ultrasonic waves can penetrate only poorly through bone or lung tissue. In this connection, it is known to mount ultrasonic directional elements and transducers at the distal end of probe tubes. These usually flexible probe tubes or catheters can be introduced into the patient and the examination can be performed intracorporeally.

In medicine, such ultrasonic probes are combined with a large number of treatment devices. U.S. Pat. No. 4,887,605 describes, for example, a catheter for laser angioplasty wherein an optical fiber is arranged for the transmission of laser light. The sonic head (directional element with transducer) at the distal end makes it possible to control a laser ablation process.

Combination of sonic probes with endoscopes (endosonographs) is especially advantageous. The sonic probe can supplement the endoscope, as known from European Patent 00 46 987. In this reference, the sonograph serves for determining the distance of the aimed-at object from the observation window so that its size can be accurately determined. The sonograph can also be an independent diagnostic device of the endosonograph. By means of an introduced sonic head, it is possible, for example, to examine the opaque tissue surrounding the probe head while, with the use of the endoscope, the probe head is precisely positioned in the patient. In most cases, the endoscopes are operated in linear sight and the sonographs in lateral sight; however, there are many other designs. For example, in European Patent 00 61 332, an endosonograph is disclosed wherein an additional peripheral window for optical lateral viewing is located at the probe head.

In order to attain local resolution with the ultrasonic probes, several processes can be considered. DOS 3,910,336, for example, describes a sector scanning method: The cylindrical probe head has a window in the peripheral direction, for radial ultrasonic beams, permitting an azimuthal sector scan about approximately 360°. However, for this purpose electrical drive means are required in the probe head whereby the probe head becomes relatively cumbersome; such probes can be used for examinations of the gastrointestinal tract. The probe can also be rotatable from the outside by way of a hollow shaft, for example, as known from DOS 3,816,982.

The conventional sonic heads (directional elements with transducers) of the ultrasonic probes exhibit considerable disadvantages, for example for intracorporeal applications:

Ultrasonic transducers are temperature-sensitive. Thereby, problems are encountered with regard to sterilizability.

Ultrasonic transducers (frequently piezoceramic elements) develop heat within the probe head; this heat is difficult to remove due to the compact structure.

The probes are relatively thick; for this reason, their utilization, for example, in arthroscopy and bronchoscopy is considerably restricted.

The operation of the transducers requires relatively high electrical voltages. Therefore, the transducers must be well insulated. If it is necessary for the probe heads to be of the type that can be opened, for example for cleaning purposes, then there are cracks through which body fluid can enter and cause short-circuiting.

In order to solve these problems, it is suggested, for example, in DOS 3,219,118 to mount special electrical contacts at the probe head, making it possible to effect a simpler mechanical exchange of components. DOS 3,537,904 proposes to decouple the ultrasonic transducer in the probe head from the control and display units. This decoupling is to take place inductively, capacitively, or via optical couplers. These devices, however, have not overcome the deficiencies in catheter-guided sonography.

U.S. Pat. Nos. 4,407,294, 4,428,379 and 4,431,006 describe, for example, lancets designed as hollow needles which are inserted by puncturing through the skin, sound conductors, preferably of steel, being introduced into such lancets and pushed through to the tip in order to examine the tissue at the tip. It is difficult with the use of this method to obtain ultrasonic images—for investigating expansive structures, the lancet would have to be newly applied for each examination point. Furthermore, a problem resides in acoustically decoupling the lancet and the sonic waveguide—due to sonic overcoupling, the signals are falsified, for example. For this reason, sound-absorbing layers are arranged in the hollow needle; thereby, the needle becomes thick, and its usefulness is restricted. Furthermore, the sound conductor is too rigid and too short to be utilized in catheters.

WO PA 87 01 269 describes a process for the transmission of ultrasonic images wherein sound waves are transmitted with fibers and/or fiber bundles from a transducer outside of the body to an organ inside the body, and the reflected waves are again transmitted back. Under the prerequisite that the fiber and/or the fiber bundle contacts the organ to be examined, this process is suitable, at best, for investigating the thin layer of tissue directly adjoining the fiber end and/or the fiber bundle end. The examination of depth structures, however, is impossible. Images with areal expansion could be obtained only by the use of fiber bundles wherein the area that can be imaged is limited by the cross-sectional area of the fiber bundle. One disadvantage in the fiber bundle design resides in that the sound wavelength, in the indicated frequency range of less than 10 MHz, is still so large that a strong over-coupling of sonic energy takes place between the fibers of the bundle, destroying the image information. It has furthermore been found that a very strong damping and dispersion of sonic energy occur in fiber bundles, due to the relative movement of the fibers.

The invention is based on the object of providing an ultrasonic probe with high local resolution and great depth focus, which is electrically safe, exhibits only minor evolution of heat in the probe head, and permits a compact structure. The ultrasonic probe is to be suitable, in particular, for use in medical sonography.

SUMMARY OF THE INVENTION

In view of the aforementioned object and other objects, the instant invention contemplates an ultrasonic process comprising at least one ultrasonic directional element in the probe head at the distal end of the probe. The probe includes at least one ultrasonic transducer located in an operating unit at the proximal end thereof and at least one sonic waveguide capable of transmitting sound waves having a carrier frequency $f_o$ of between 450 kHz and 28 mHz for the transmission of sound waves from the ultrasonic transducer to the directional element. In accordance with the invention, the diameter D of a sonic waveguide with a circular cross-section and, respectively, the maximum value ($D_{max}$) and the minimum value ($D_{min}$) of a chord through the cross-sectional surface of a sonic waveguide with a non-circular cross-section ranges from between 20 μm and 1000 μm, wherein the following parameters apply for the product from the diameter D of a sonic waveguide having a circular cross-section and, respectively, the maximum $D_{max}$ (in which case $D=D_{max}$) of the chord through the cross-sectional surface of a sonic waveguide having a non-circular cross-section and the carrier frequency $f_o$ of the sound waves:

$D \cdot f_o \leq 7000$ m/s if the sonic waveguide consists of materials with a Poisson ratio $v$ smaller than 0.20, and $D \cdot f_o \leq 4200$ m/s in case of other materials, if axial waves are transmitted and $D \cdot f_o \leq 14,000$ m/s for SWG based on Be, $D \cdot f_o \leq 6100$ m/s for SWG based on silica glass, and $D \cdot f_o \leq 5100$ m/s for SWG of other materials, if torsional waves are to be transmitted.

BRIEF DESCRIPTION OF THE DRAWING

Various other objects, features, and attendant advantages of the present invention will be more fully appreciated as the same becomes better understood when considered in conjunction with the accompanying drawing in which like reference characters designate the same or similar parts throughout the several views, and wherein.

DETAILED DESCRIPTION

Figure 1:
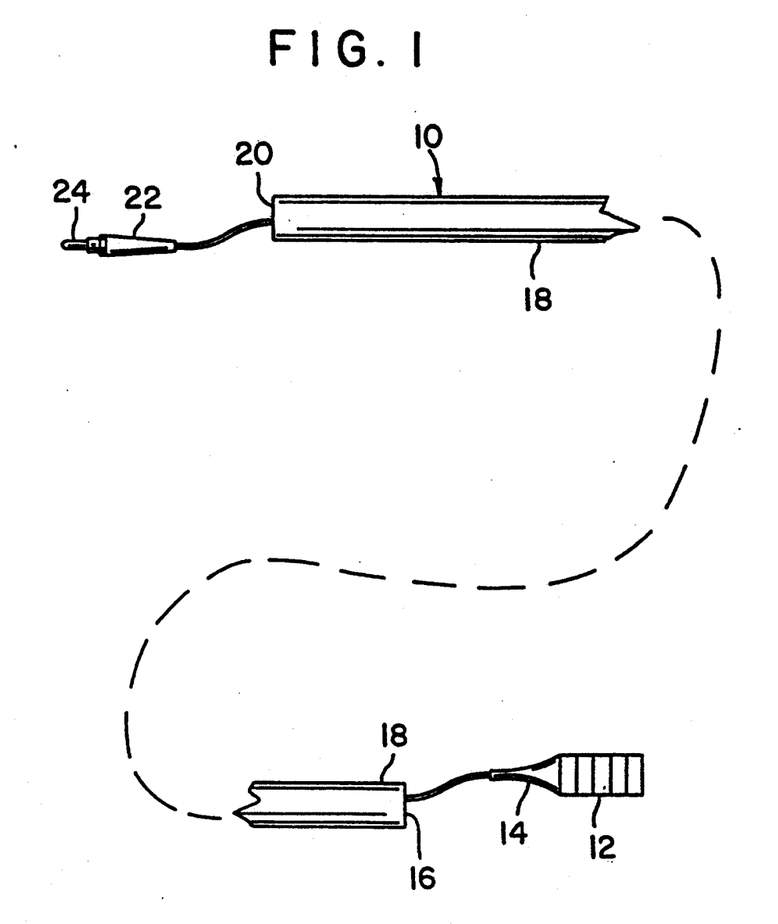
FIG. 1 is a diagrammatical view of an ultrasonic probe configured in accordance with the principles of the instant invention.
Figure 2:
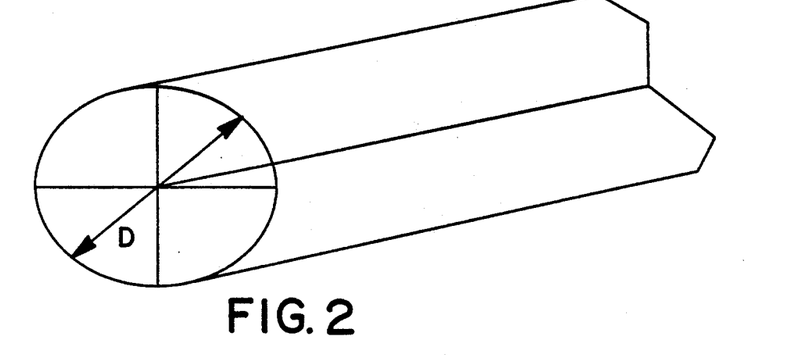
FIG. 2 is a schematic view of a waveguide with a circular cross-section.
Figure 3:
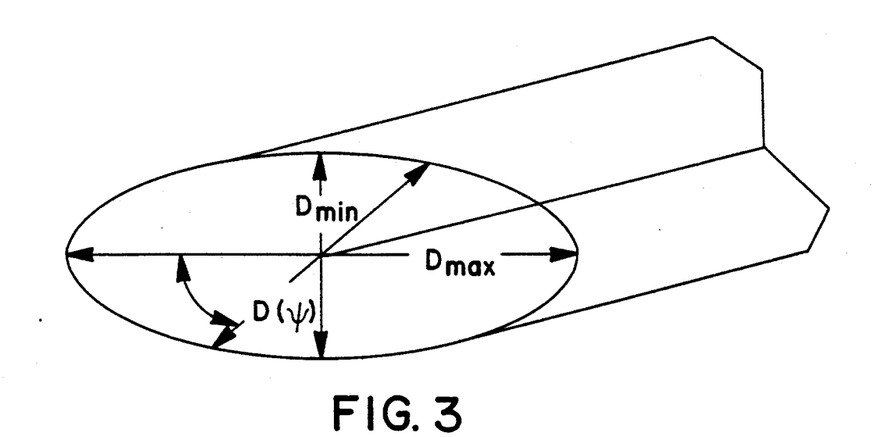
FIG. 3 is a schematic view of a waveguide with an elliptical cross-section.

Referring now to the drawing figure, there is shown an ultrasonic probe arrangement, designated generally by the numeral 10, comprising an ultrasonic transducer 12, which is connected by a first flexible sonic waveguide 14 to a first end 16 of an image dissector tube 18. The image dissector tube 18 is connected at a second end 20 by a second flexible sonic waveguide 22 to an ultrasonic connecting element 24 on the image dissector head. The aforedescribed structure 10 utilizes the parameters and materials of the instant invention described below.

In the ultrasonic probe according to this invention, the sound waves are produced by transducers 12 at the proximal end of the probe and are transmitted via suitable sonic waveguides (SWG) 22 to directional elements at the distal end of the probe 24 (probe head). Ultrasonic probes with directional elements connected with transducers via sonic waveguides are unknown in the state of the art. There has been the silent technical rule that SWG are unusable for ultrasonic probes on account of the dispersion and damping occurring in these SWG's. Therefore, it is the more surprising that it has been possible to discover, for the ultrasonic probe according to the invention, even several usable structural types for SWG's.

In the ultrasonic probes employed in practice, the directional element is always in direct contact with the transducers in order to reduce damping and dispersion of the sound waves. At best, a short "lead path" exists between directional element and transducer. This lead path can permit, for example, a simpler separation of the reflected signal from the incident one, for example when the signals are lengthened in time by building-up or decay processes in the transducer. Although these lead paths are, at most, of a length of a few cm, they can hardly be considered for intracorporeal medical applications, for example, because the required compact structural designs cannot be achieved thereby. Lead paths in technology are relatively thick; their diameter amounts to several mm.

The use of the SWG's 14 and 22 designed in accordance with this invention ensures that even very brief sound pulses can be transmitted without effective damping or effective chronological or frequency distortion. The diameter of the sonic waveguide according to this invention is, however, so small that the sonic waveguide itself does not exhibit a directional action. For this reason, it is necessary to use a directional element at the probe head. The directional element furthermore has the task of promoting coupling of the sound waves to the medium to be examined—sonic waveguides normally do not permit an efficient coupling to the medium to be studied.

Removal of the transducers from the probe head has the advantage that electrical leads to the probe head are unnecessary. The probe is thereby electrically safe, and heat production in the probe head is low. The transducers need not be taken into account when constructing the directional elements: Thereby it is possible to accommodate directional elements having a high directional activity even in a narrow probe head. Scanning can take place by means of suitable mechanical, pneumatic, and similar devices in the probe head. The probes can be designed thinner and are suitable for utilizations in narrow vessels. Using the sonic waveguides 14 configured in accordance with the invention ensures that even very short sonic pulses may be transmitted without effective chronological or frequency distortion.

In the simplest case, the sonic waveguide 14 lies unprotected within the body. In such a case, increased transmission losses can be expected due to lateral decoupling of sound from the SWG into the surrounding body tissue. Normally, these losses are too high. The SWG 14 is therefore guided in most cases in a so-called probe tube (not shown). The probe tube can be stiff or flexible. This probe tube can be, for example, one of the many known medical catheters or a free endoscoping duct of a medical catheter; in certain circumstances, a simple hose can be enough.

The length of the SWG 14 according to the invention is at least 8 cm, but at most 5 m. A length of more than 8 cm has several advantages; for example, the SWG 14 can then serve additionally as a lead path, perhaps to effect a simpler separation of the reflected signal from the beamed-in signal (e.g. during building-up and decay processes). A length of less than 8 cm is also hardly required, even in case of medical applications. However, if this can be managed, the length of the SWG 14 should amount to at least 30 cm because then handling of the probe becomes simpler.

A length of 5 m is entirely sufficient even for specific technical applications under extreme conditions, for example in case the probe head is exposed to strong irradiation or strong thermal stress. With a length of more than 5 m, the SWG 14 usually can hardly be used any more; in most instances, the dispersion and absorption of the sonic pulses become too strong, or the repetition frequency of the sonic pulses must be too greatly reduced on account of the long transit time of the sonic pulses. However, the use of shorter SWG's generally leads to improved properties of the SWG. For this reason, insofar as this can be managed, the length of the SWG for technical applications should amount to at most 3 m and for medical applications less than 2 m.

Most of the conventional ultrasonic transducers and ultrasonic directional elements are suitable for the ultrasonic probe of this invention. In contrast thereto, greater care must be applied to the selection of suitable sonic waveguides.

An SWG is known from DOS 1,947,968 consisting of a bundle of thin (carbon) fibers, the end surface of which is designed so that the bundle as a whole has a sound-focusing effect. A use for this fiber bundle is not disclosed. The disadvantages of fiber bundles in the aforedescribed utilization have been discussed above.

The transmission of sound presupposes investigations of the effects determining sound transmission. Systematic considerations on elastic waves in fibers and, respectively, cylinders can be found in L. Pochhammer, "Über die Fortpflanzungsgeschwindigkeiten kleiner Schwingungen in einem unbegrenzten isotropen Kreiszylinder" [On the Propagation Velocities of Small Vibrations in an Unlimited Isotropic Circular Cylinder], J. Math. 81: 324 (1876); E. Sittig, "Zur Systematik der elastischen Eigenschwingungen isotroper Kreiszylinder" [On the Systematics of the Elastic Natural Vibrations of Isotropic Circular Cylinders], Acustica 7: 175 (1957), and R. N. Thurstson, "Elastic Rods and Clad Rods", J. Acoust. Soc. Am. 64: 1 (1978).

U.S. Pat. No. 3,315,663 discloses a bronchoscope containing an SWG. With this SWG, sonic waves of about 20 kHz are to be introduced into the bronchi in order to loosen the phlegm stuck therein.

U.S. Pat. No. 3,368,085 describes a taper called "amplifier horn" suitable for coupling sonic waves into an SWG upon suitable dimensioning. Although the patent indicates metals as materials for the taper, the taper can, in principle, also consist of other substances, for example of glass.

U.S. Pat. No. 3,736,532 discloses SWG's for low-dispersion signal transmission. The waveguide is surrounded by sound-absorbing layers in order to shield the sonic wave. These layers, however, greatly attenuate the guided sonic wave because the evanescent wave penetrates into the absorber. In another embodiment, surface or interface waves are utilized for transmitting the sonic wave—but such SWG's function only at extremely high frequencies (the sonic wavelength must be smaller than the thickness of the layer guiding same). Flexible SWG's are also known exhibiting a core and a jacket with differing elastic properties, for example from U.S. Pat. No. 3,824,505 or 3,922,622. These SWG's are to function like optical core-jacket fibers, i.e. the sonic wave is to be enclosed in the core and isolated from the effects of the surroundings. For this purpose, the thickness of the jacket, however, would have to be a multiple of the sonic wavelength. At the typical dimensions of flexible fibers, very high frequencies would be required for this purpose; one must start with $\geq 100$ MHz; these frequencies are too high for sonography.

Furthermore, the known SWG's have the characteristic that the sonic waves therein are in radial or azimuthal modes, the geometric dispersion of which is small. However, it has been found that these modes cannot transmit any sonic waves of higher power, and that their coupling in and coupling out operations are too difficult under practical conditions.

Also, optical fibers have been known for laser spectroscopy utilization into which optical and acoustic waves are coupled. By acousto-optic interactions between the waves, the frequency of the optical wave is shifted by an integral multiple of the acoustic wave. In order to attain significant frequency shifts, however, the sonic frequency must be extremely high. The fibers, generally thin optical monomode fibers, can transmit only low sonic power over short distances because they are adapted to the coupling in and transmission of optical waves.

The invention can be realized, in principle, with a plurality of materials for the SWG's. Advantageously, the selection of a suitable material will be made in dependence on the problem involved.

Many materials which would have advantages theoretically, for example due to their mechanical data (e.g. beryllium with a sonic velocity of 12.5 km/s and a Poisson ratio of merely 0.1, or the chalcogenide glasses with a very low ultrasonic absorption), are eliminated because of their toxicity or lack of machinability. SWG's from beryllium, however, could be definitely considered for technical usages wherein contact with the SWG is precluded. In the medical field, for example, SWG's from Au alloys or Pt alloys would be suitable, but these materials normally exhibit inadequate strength. Copper, brass, bronzes, and similar materials, though easy to machine, usually exhibit a coarse-grained structure that can lead to considerable ultrasound absorption (which in most cases increases due to storage or aging); these materials are therefore to be excluded usually, on account of unfavorable mechanical properties (besides toxicity). Besides, problems can occur in case of metallic SWG's due to electrical conductivity—in such instances, the use of SWG's of glass would basically present itself.

A person skilled in the art will select the materials for the SWG suitable for a specific usage by virtue of the dimensioning rules in this patent disclosure and based on his experience. Yet, materials will be proposed hereinbelow for SWG's with which the problem can be solved in the simplest way and with which almost all cases of application can be covered.

The most strongly preferred material is silica glass ($SiO_2$ glass) as utilized for the optical fibers. This is a glass consisting, except for negligible admixtures, of $SiO_2$, $GeO_2$, $B_2O_3$, $P_2O_5$ and $TiO_2$. This glass exhibits the best data based on the sum total of its properties, such as strength, elastic parameters, sound absorption, and electrical resistance. It can be utilized without problems in the medical field. Similar considerations apply with regard to the conventional technical and optical glasses which are likewise preferred as a material for the SWG. The production of molded articles and/or fibers with varying profiles and dimensions at high precision from glass or silica glass is known, for example, from the optical communications technology.

Tungsten alloys and titanium alloys likewise show good properties, e.g. high strength and low ultrasound absorption. Both materials can be utilized in the medical area without any great problems. Alloys of steel, Mg and Al (and further light metal alloys), though exhibiting in total poorer mechanical properties and relatively high ultrasound absorption, can be machined in a simpler way than W alloys or Ti alloys. For this reason, they are likewise included in the preferred choice for SWG materials.

The SWG of the ultrasonic probe according to this invention has an outer diameter D, called simply diameter in the following, which is larger than 20 $\mu$m and smaller than 1,000 $\mu$m. For an SWG with a noncircular cross section, the diameter is considered to be the chord $D(\psi)$, dependent on the azimuthal angle $\psi$, of the SWG cross-sectional surface through the apex of the angle $\psi$. The apex here lies in the axis of symmetry of the SWG (usual coordinate system). Then the smallest value for $D(\psi)$ is to be larger than 20 $\mu$m, and the largest value for $D(\psi)$ smaller than 1,000 $\mu$m. This ensures that the SWG has adequate strength and a flexibility sufficient for use in probe tubes and/or catheters. Thinner SWG's no longer exhibit adequate tensile strength, and thicker ones have too high a flexure stiffness. With these dimensions, the SWG can still be called flexible in the usual sense (as in the optical fibers).

The use of SWG's having a noncircular cross section is preferred, for example, in case a torsional movement of the SWG which can, for example, raise the dispersion, is to be suppressed. In case of SWG's having a noncircular cross section, the ratio of the maximum value $D_{max}$ to the minimum value $D_{min}$ should be at least 1.4, particularly for the chord $D(\psi)$, dependent on the azimuthal angle $\psi$, through the cross-sectional surface. As a result, the SWG will spontaneously twist, under the influence of a bending moment based on its directionally dependent flexural stiffness, in such a way that the flexure of the SWG takes place about an axis in parallel to the direction with the maximum value of the chord. It is advantageous, in particular, for the directions having the maximum value and the minimum value for the chord to be disposed perpendicularly to each other. Therefore, the flexural stiffness of the SWG effective for this flexure, which then determined by the short chord, is especially low. Thereby, the objective can be achieved that an SWG with a high strength, i.e. a large cross-sectional surface, yet exhibits a low flexural stiffness for the flexure.

In general, however, the drawbacks predominate in SWG's having an irregular cross section. In SWG's having a noncircular cross section, there are, for examples, always axes having an unfavorable proportion of flexural stiffness to cross-sectional surface. Shear flexural waves can then be readily generated with respect to the direction having the low flexural stiffness. In all applications wherein, for example, coupling of the sound waves with torsional waves is of lesser significance, SWG's having a circular cross section are preferred (except for cross-sectional fluctuations caused by the manufacturing process). In case of an SWG having a circular cross section, though, one does not find an axis having a lower flexural stiffness. For this reason, the SWG, in total, can have a lower flexural stiffness. Therefore, a diameter of less than 800 μm is preferred for an SWG having a circular cross section.

For an SWG having a circular cross section, a number of mass-produced components known in the fiber optic field could be usable, such as plugs, hoses, lead-throughs, etc., if the SWG's exhibit standard sizes. In order to be able to use these components, it is recommended that the outer diameter of the SWG's ranges from 60 μm to 600 μm.

The SWG of the ultrasonic probe according to this invention is to be suitable for the transmission of axial waves. In case of axial waves, the SWG vibrates predominately in the direction of its axis. Thereby a high coupling-in and coupling-out efficiency for sound waves can be attained at the SWG ends. Furthermore, when dimensioning and using the SWG's in accordance with this invention, the transmission losses by coupling out and the distortion of the sonic pulses due to dispersion are low.

Unavoidably, a movement of the SWG material in the radial direction will also take place in case of axial waves: On the one hand, the axial movement is always accompanied by a radial vibration of the SWG due to transverse contraction of the material; on the other hand, axial waves represent a borderline case of the so-called axial-radial waves—axial waves can, under unfavorable conditions unfortunately prevailing during the typical usage applications, easily change over into another borderline case, so-called radial waves. In the radial waves, the radial movement of the SWG predominates (a type of shear waves). Thereby, sonic energy from the SWG is very extensively coupled into the surrounding medium, and the guided sound wave is attenuated, or a strong effect is exerted on the propagation conditions of the guided sound wave through the surrounding medium. The resultant additional dispersion and pulse distortion are uncontrollable.

It has been found that these effects depend on the Poisson ratio $\nu$ (transverse contraction number) of the fibrous material. In this connection, it was surprisingly discovered that all potential fiber materials can be grouped into two categories, namely into those wherein $\nu < 0.20$ (among these are $SiO_2$ with $\nu \approx 0.17$ to 0.19, W alloys with $\nu \approx 0.17$, and Be alloys with $\nu \approx 0.10$), and into those wherein $\nu \geq 0.20$ (among these are "normal" glasses with $\nu \approx 0.25$ and "normal" metallic materials with $\nu \approx 0.29$ to 0.39, dependent on the processing, pretreatment, and alloy), different conditions being found for these categories:

In order to avoid radial movement (changeover into radial waves), the following applies preferably for the product from the SWG diameter D (for noncircular SWG's, the largest value of the chord) and the carrier frequency $f_o$ of the sound waves:

$$D \cdot f_o \leq 7,000 \text{ m/s}$$

if the SWG consists of materials with a Poisson ratio $\nu$ smaller than 0.20, otherwise:

$$D \cdot f_o \leq 4,200 \text{ m/s}$$

The SWG properties can be still further improved by maintaining even smaller limit values for the $D \cdot f_o$ product (i.e. by selecting smaller values for the diameter at a given carrier frequency). Therefore, more preferred for SWG's are the following values:

$$D \cdot f_o \leq 3,000 \text{ m/s}$$

if $\nu < 0.20$ otherwise:

$$D \cdot f_o \leq 1,700 \text{ m/s}$$

In case of SWG's consisting of several materials, these materials, under practical conditions, exhibit a similar Poisson ratio (e.g. $SiO_2$ glasses having a slightly different doping, alloys with a low variation within the same class of metals)—otherwise, the composite of the materials would not exhibit the required strength. Therefore, a uniform Poisson ratio $\nu$ can usually be assigned to the fibrous materials. If there is an SWG, after all, having materials of greatly differing mechanical effects, the highest Poisson ratio is to be considered in the above-mentioned dimensional directions.

Maintaining the above-indicated conditions (upper limits for $D \cdot f_o$ in dependence on $\nu$) leads to the additional positive effect that the difference between the group velocity of the waves and the phase velocity becomes negligibly small under practical conditions. The phase velocity $c_a$ of the axial waves then is, in an approximation:

$$c_a/c_o \approx 1 - 4.5 \cdot \nu^2 \cdot \left(\frac{D \cdot f_o}{c_o}\right)^2$$

$[c_o = \sqrt{(E/\rho)}]$ is the sonic velocity for longitudinal waves in a thin rod; $\nu$, E and $\rho$: Poisson ratio, modulus of elasticity, and density of the SWG material; for SWG's composed of several materials, effective values and the group velocity are to be inserted here:

$$g \approx c_a^3/c_o^2$$

(for phase and group velocities there are no compact expressions). Consequently, calculation of the sonographs becomes simpler, which is a decisive advantage in practice.

Another advantage resides in that coupling to surface waves or interface waves (e.g. Rayleigh or Love waves) becomes small. In contrast to known ultrasonic delay lines using precisely surface or interface waves, it proved to be advantageous in case of the SWG's to prevent any coupling to these waves: Surface or interface waves are accompanied by extensive decoupling and dispersion which latter furthermore depends in an uncontrollable manner on the properties of the surrounding medium. In these waves, the sonic energy is transported in a thin layer of the SWG material; thus, these waves cannot transmit the necessary sonic power, either.

When sound is coupled in, it is in certain cases difficult to generate pure axial waves. On account of differing ultrasonic impedances (for example, $\sqrt{E\cdot\rho}$ for axial waves and $\sqrt{G\cdot\rho}$ for shear waves, G: shear modulus) at transition points, the observation is made usually even with low sonic outputs, perfect radial symmetry, and perfect axial excitation that radial waves also occur in all cases even though with a markedly lower amplitude than in case of the axial waves. Normally, especially at higher sonic outputs, shear or bending waves are likewise produced in the SWG (again with a markedly lower amplitude), due to deviations from the radial symmetry, e.g. small tilting of components due to the manufacturing process, strong bends or kinks along the extension of the SWG. Here, the effect can be positively exploited that, in the SWG according to the invention, the radial, shear and bending waves are more effectively damped by coupling out than the axial waves so that these waves are negligible in case of longer transmission paths. If too great an excitation of these waves should yet occur, a lowering of the sonic output is in most cases a remedy. It is also possible to attach devices to the SWG which specifically damp radial, shear and bending waves (such devices for the shear bending waves will be described further below). Also, the ultrasonic directional elements at the distal end of the ultrasonic probe can furthermore be designed so that only axial waves will become effective. This embodiment is especially recommended with short SWG's.

The SWG of the ultrasonic probe according to this invention is to be suitable for the transmission of torsional waves. In torsional waves, the SWG vibrates in the azimuthal direction (cylinder coordinates). They represent likewise a type of shear waves, running without transverse contraction and/or radial movement through the SWG; the Poisson raio of the fiber material is of no importance for torsional waves. With a dimensioning and utilization of the SWG according to the invention, the transmission losses and the distortion of the sound waves on account of dispersion are likewise low. For transmitting torsional waves, SWG's having a circular cross section are preferred because in such a case the transmission losses due to coupling out (or coupling to the surrounding medium) are at a minimum.

The torsional waves can be degenerate, i.e. several torsional modes can occur at the same frequency. Since these torsional modes exhibit similar symmetry characteristics, the sonic energy can readily couple over between them. On account of this mode coupling, the dispersion of the torsional waves can increase. For this reason, it is preferred that the SWG is single-wave with respect to the transmission of torsional waves (monomode, only the torsional fundamental wave is transmitted). For this purpose, the following is to be established:

$f_o\cdot D \leq 14,000$ m/s for SWG based on Be,
$f_o\cdot D \leq 6,100$ m/s for SWG of silica glass, and
$f_o\cdot D \leq 5,100$ m/s for SWG from other materials
(smaller-equal relationship; $f_o$: carrier frequency of the sound waves, D: diameter of SWG). The differences for the upper limits for $f_o\cdot D$ result from the greatly differing sonic velocities for the torsional waves in the media.

When maintaining the previously recited conditions, no dispersion occurs in a (stretched) SWG with an approximately circular cross section; in other words, the sonic velocity of the torsional fundamental wave is independent of the frequency and amounts to $c_t = \sqrt{G/\rho}$ (G: shear modulus; $\rho$: density of the fiber material; $c_t$ thus is the sonic velocity of shear waves known from elementary mechanics). This is of special advantage in the transmission of short sonic pulses.

The torsional waves of a higher order show strong dispersion and normally are unsuitable for the transmission of short sonic pulses.

The torsional fundamental wave, however, has the property that therein the azimuthal movement of the SWG increases from the inside toward the outside, i.e. its azimuthal movement is greatest on the surface: The SWG material is actually poorly utilized with the torsional fundamental wave; for this reason, the torsional fundamental wave is less suitable than the axial waves, as a rule, for the transmission of higher-power sound waves.

Increased transmission losses can occur, in particular, in case the SWG is in a highly viscous medium (e.g. a rinsing fluid in a catheter), on account of the strong azimuthal movement of the SWG. Experience has shown that the coupling out losses of an SWG can be reduced for torsional waves by reducing the SWG diameter. For this reason, the following relationships are more strongly preferred:

$f_o\cdot D \leq 8,000$ m/s for SWG on Be basis,
$f_o\cdot D \leq 4,200$ m/s for SWG made of silica glass, and
$f_o\cdot D \leq 3,000$ m/s for SWG made of other materials.

The solution of the problem requires to tune the SWG's precisely to the applications. This is possible in connection with the SWG's of this invention for applications wherein examinations are to be conducted according to the pulse echo method or according to the Doppler method if the carrier frequency $f_o$ is higher than 450 kHz and lower than 28 MHz.

By the limitation to the frequency range of more than 450 kHz, the guided sound waves are prevented, in case of disturbances of the ideal SWG extension, for example at bends, from changing over, for example, spontaneously into so-called bending waves (upon the excitation of axial waves). Bending waves are unsuitable for the transmission of sound waves along the lines of this invention because they are accompanied by strong damping due to the excessive lateral movement, and because their dispersion (sonic velocity $\sim \sqrt{f_o}$) is much too high for the transmission of short sonic pulses. By the limitation to frequencies of less than 28 MHz, coupling to surface or interface waves, with the aforedescribed disadvantages, is even more greatly reduced.

For the transmission of sound waves in a frequency range from 800 kHz to 20 MHz, the ultrasonic probe can be of an especially simple structure. With a frequency of less than 800 kHz, it could happen that during bending of the SWG a contribution toward the sonic velocity occurs in dependence on the bending because, for example, the axial forces effective in the SWG in case of axial waves excite a stationary vibration of the bent SWG segment. The bending-dependent sonic velocity for axial waves in the SWG's of this invention amounts, in an approximation, to $$c(f_o) \approx c_0[1 + 0.013\cdot(\lambda/R)^2]$$

(R: bending radius; λ: sound wavelength in the fiber; $\lambda \approx c_o/f_o$; $c_o$: sonic velocity in the stretched SWG.) If the frequency becomes too low, the transit time of a sonic pulse, for example, can be too much dependent on the bending radius—in ultrasonic technology, such transit time effects, which do not lend themselves to control, can hardly be taken into account in evaluation. If the frequency exceeds 20 MHz, the design of ultrasonic transducers having suitable coupling in and coupling out elements for the SWG becomes difficult under practical conditions, for example on account of the short wavelengths.

The frequency range that can be covered by the SWG's of this invention is larger than necessary for medical sonography (about 1 to 20 MHz). Higher frequencies do not make sense because then the damping of the ultrasonic waves in the biological tissue would be too strong [the absorption coefficient of most types of tissues for ultrasonic waves increases approximately as a square of the frequency and is approximately 0.2 ... 2.5 dB/cm·$(f_o/MHz)^2$]. Lower frequencies would not be practical, either, because the spatial resolution of the sonograph is proportional to the sound wavelength and thus reciprocal to the sonic frequency ($\lambda \approx c_o/f_o$; the sonic velocity $c_o$ of most types of tissue is 1,450 to 1,650 m/s).

Normally, the SWG's are to be flexible, i.e. are to be bendable to a radius intended for the respective utilization. Minimum flexibility of the SWG's is advantageous even when used in rigid probe tubes, for example because in such a case the guidance of other elements in the probe tube becomes simpler. In rigid probe tubes, a minimum bending radius of 10 ... 30 cm is generally sufficient. However, flexible probes for technical or medical applications pose markedly stricter requirements; in this case, a bending radius of 2 ... 5 cm, sometimes of less than 2 cm, may be needed. For an estimate of the dimensioning of the SGW's, it is enough to start with relatively stiff SWG's, called hereinbelow "stiff SGW's", with a minimum bending radius of $R \approx 10 ... 30$ cm, and with "flexible SWG's" having a minimum bending radius of $R \approx 2 ... 5$ cm.

Thereby, additional limitations are provided for the SWG diameter: On the surface of an SWG, bent at the radius R, of a material having the modulus of elasticity E (in case of SWG's of several materials, the modulus of elasticity of the material of the outermost layer), with the diameter D (in case of SWG's of a noncircular cross-sectional profile, the diameter in the plane including the bending circle tangent on the SWG's), the normal stress (tensile or compressive stress in the direction of the SWG axis) amounts, for example, to $\sigma_{max} \approx 0.5 \cdot E \cdot (D/R)$. To this stress are added the stresses evoked by the guided sonic wave, but these stresses are generally substantially lower than the bending stresses.

The resultant mechanical stress must, of course, be lower than the yield stress, ultimate tensile stress or ruptural stress of the SWG material. However, still stricter limits must be maintained for the SWG's according to this invention: $\sigma_{max}$ must be smaller than the maximum stress up to which the material exhibits an elastic behavior at all (no permanent deformation of the material after the stresses have disappeared), and for applications wherein an especially frequency-pure transmission is important, e.g. in Doppler sonography, the stress is to be even lower than the characteristic limit stress of the material up to which the material shows a linear-elastic behavior (up to which a linear correlation is found between stress and deformation—Hooke's law). If this limit is exceeded, a frequency conversion (for example mixing of sum or difference frequencies) or coupling over of sonic energy to other modes can, for example, occur in the SWG.

Unfortunately, the limit up to which a material shows a linear-elastic behavior is blurred: In the potential materials, a deviation from the linear-elastic behavior is observed even for very low stresses. On the other hand, this nonlinearity in most cases does not have any direct effect because, for example, a bending-induced dispersion of sound waves occurs, preventing a coherent interaction between various sonic modes or sound waves with differing frequency (no constructive overcoupling based on too short a period of interaction). A number of mechanisms has been found enhancing or preventing the described effects. The effects in detail cannot be taken into account, but rather simple rules of thumb must be applied.

In SWG's of relatively ductile Ag alloys, Au alloys or Pt alloys (modulus of elasticity E for Ag: $\approx 81$ GPa, Au: 80 GPa and Pt: 173 GPa; 1 GPa = $10^9$ Pa), the bending stress on the SWG surface must be lower than 90 MPa ($\approx 9$ kp/mm$^2$; 1 MPa = $10^6$ Pa). For this reason, these materials can only be considered for stiff SWG's (minimum bending radius of $R \approx 10 ... 30$ cm); for the SWG diameter, a value of less than $D \leq 250$ μm is preferred. If larger fiber radii were to be attained, or if the SWG were to be bent at a greater extent, then the materials would have to be alloyed more extensively; in such a case, a higher ultrasonic absorption would have to be tolerated for these materials.

In SWG's of Fe alloys or steel alloys (modulus of elasticity $E \approx 210$ GPa), the bending stress on the SWG surface is to be lower than 180 MPa. For this reason, a diameter of $D \leq 200$ μm is preferred for stiff SWG's ($R \approx 10 ... 30$ cm), and a diameter of $D \leq 80$ μm is preferred for flexible SWG's ($R \approx 2 ... 5$ cm). Although a higher tensile strength is obtained in these materials than in case of noble metal alloys, high tensile stresses will always appear on the surface of such fibers due to the higher E modulus.

This holds true to an even greater degree for SWG's made of W alloys ($E \approx 400$ GPa). Here the bending stress on the SWG surface is to be lower than 200 MPa. For this reason, a diameter of $D \leq 200$ μm is preferred for stiff SWG's ($R \approx 10 ... 30$ cm), and a diameter of $D \leq 50$ μm is preferred for flexible SWG's ($R \approx 2 ... 5$ cm). In the case of W alloys, the production of very thin SWG's with narrow tolerances has been known.

In SWG's of Mg alloys or Al alloys ($E \approx 40 ... 70$ GPa), the bending stress on the SWG surface is to be lower than 100 ... 120 MPa. For this reason, a diameter of $D \leq 300$ μm is preferred for stiff SWG's ($R \approx 10 ... 30$ cm), and a diameter of $D \leq 160$ μm is preferred for flexible SWG's ($R \approx 2 ... 5$ cm). In these materials, the low modulus of elasticity has a positive effect. The relatively low ruptural stress of these materials is not attained because the tensile or compressive stresses on the SWG surface are low due to the low E modulus.

In SWG's made of Ti alloys ($E \approx 105$ GPa), the bending stress on the SWG surface is to be lower than 200 MPa. Therefore, for stiff SWG's ($R \approx 10 ... 30$ cm), a diameter of $D \leq 300$ μm is preferred, and for flexible SWG's ($R \approx 2 ... 5$ cm), a diameter of $D \leq 120$ μm is preferred. In case of SWG's of these materials, there is the positive effect that here a low E modulus and a high tensile strength converge.

In SWG's of glasses (normal technical or optical glass or silica glass, $E \approx 72 \ldots 80$ GPa), the bending stress on the SWG surface is to be lower than 500 MPa. Thus, for flexible SWG's ($R \approx 2 \ldots 5$ cm), an SWG diameter of $D \leq 350$ μm is preferred. (For larger bending radii, no limitations exist.) As compared with the metals, a markedly larger permissible SWG diameter value was surprisingly found for glasses. In our opinion, this can be traced back to the relatively low modulus of elasticity (consequently the mechanical stresses on the SWG surface are low) and to the microscopic structure of the glasses: glasses have a homogeneous structure whereas metals are polycrystalline. Thus, in metals, microscopic movements of the microcrystallites can occur even at relatively low mechanical stresses (rupturing of grain boundaries, slippage), impossible in glasses. For this reason alone, it is advantageous to manufacture the SWG's from glasses.

On account of the absorption of sonic energy by the SWG material (intrinsic sound absorption), transmission losses are encountered. Therefore, at the end of the SWG, the sonic signal can have been weakened to such an extent that it is no longer usable for measurement purposes. The intrinsic sound absorption of the SWG's depends on the SWG material employed, the transmission length L, and the carrier frequency $f_o$.

Unfortunately, it is difficult to reliably predetermine the sound absorption coefficient of a material; it depends on many influential variables. In polycrystalline materials, for example, a contribution occurs that can be traced back to scattering (similar to Rayleigh scattering in electromagnetic radiation), increasing proportionally to the fourth power of the carrier frequency and proportionally to the third power of the average crystallite diameter. Since it is possible, for example, in metals to widely vary the crystallite diameter by the processing operation (as annealing), the ultrasonic absorption coefficient can vary greatly. Under certain circumstances, the value for a material fluctuates by more than three orders. However, the way in which a low ultrasonic absorption coefficient can be set in a material is known to material technicians.

The SWG according to this invention is fashioned so that several contributions toward ultrasonic damping, occurring in a solid piece of the respective material, will not become of significance. For example, the ratio of the sonic wavelength to the transverse dimensions is chosen so that the contribution, similar to Rayleigh scattering, toward the ultrasonic damping is small: Scattering is not isotropic but rather takes place in a focused fashion in a narrow angular range about the SWG axis. The scattering amplitude is correspondingly weakened, and ultrasonic damping is lower.

For imparting a simpler structure to the SWG, the following rules of thumb are found, based on empirical data: SWG's satisfying the following condition are preferred in order to keep sonic absorption to a low level:

$$L \cdot f_o^2 \leq K$$

($f_o$: carrier frequency, L: length of SWG), wherein the material or SWG constant K is as follows for SWG's made from

| Ti alloys, W alloys, Al alloys or Mg alloys: | $K \approx 70 \cdot 10^{12}$ m/s² |
| Ag alloys, Au alloys or Pt alloys: | $K \approx 22 \cdot 10^{12}$ m/s² |
| Fe alloys or steel alloys: | $K \approx 7 \cdot 10^{12}$ m/s² |
| Normal glasses: | $K \approx 80 \cdot 10^{12}$ m/s² |
| Silica glass: | $K \approx 1 \cdot 10^{16}$ m/s² |

The best values are observed for silica glass; in our opinion, this can again be traced back to its homogeneity. It is sufficient for most usage applications to maintain these limits. For high-resolution sonography, however, a still lower ultrasonic absorption may be needed in certain cases; then, the following is to apply for SWG's made from

| Ti alloys or W alloys: | $K \approx 2.5 \cdot 10^{12}$ m/s² |
| Al alloys or Mg alloys: | $K \approx 3 \cdot 10^{12}$ m/s² |
| Ag alloys, Au alloys or Pt alloys: | $K \approx 0.7 \cdot 10^{12}$ m/s² |
| Steel alloys or Fe alloys: | $K \approx 0.14 \cdot 10^{12}$ m/s² |
| For SWG's made of normal glasses: | $K \approx 0.8 \cdot 10^{12}$ m/s² |
| For SWG's made of silica glass: | $K \approx 1 \cdot 10^{15}$ m/s² |

On account of the high sonic frequencies required for high-resolution sonography, it must be assumed that then primarily silica glass fibers are suitable.

It has been found that high transmission losses arise by coupling of the axial waves to shear bending waves. This is so because shear bending waves are connected with very strong movements of the SWG's (under unfavorable conditions, even whiplash movements can be observed) evoking strongly elastic or viscous vibrations in the surrounding medium. Thereby, the guided sound wave loses in energy and its dispersion is increased. This effect occurs, above all, at low frequencies.

The arising of shear bending waves can in most cases be prevented by restricting the lateral movement of the SWG's by supporting elements. In this connection, the spacing of the supporting elements $L_{st}$ along the SWG axis is to be smaller than half the wavelength of the shear bending waves forming at the carrier frequency:

$$L_{st} \leq \sqrt{(520 \text{ m/s}) \cdot (D/f_o)}$$

In this context, D is the diameter of an SWG having a circular cross section or, respectively, the minimum value of the chord through the cross-sectional surface in case of an SWG having a noncircular cross section (the calculation is to include the shear bending waves with the shortest wavelength with respect to the lowest flexural stiffness of the SWG, or the smallest chord).

Under certain circumstances, no supporting elements can be mounted. In such a case, the losses produced by the lateral movements of the SWG's must be tolerated. These losses can perhaps be reduced by decreasing the transmitted sound output: The tendency toward coupling of the axial waves to shear bending waves actually grows when the sonic output of the axial waves increases.

In adverse circumstances, transit time interference effects can occur for the axial waves due to the supporting elements. In order to suppress same, the following applies $$L_{st} \geq \frac{3{,}150 \text{ m/s}}{f_o}$$

If the described supporting elements are to be attached for damping the shear bending waves, and if the SWG is to be bent about a predetermined axis during flexing of the probe tube, it is furthermore advantageous to design the supporting elements so that they enforce a bending of the sonic waveguide about the predetermined axis. Thereby, the total number of supporting elements of the SWG is reduced which, in the final analysis, expresses itself in a higher transmission efficiency of the SWG. In SWG's with a noncircular cross section, supporting elements provide the effect that during flexing of the probe tube the SWG is bent about an axis in parallel to the direction having the largest value for the chord $D(\psi)$.

In SWG's for the transmission of sonic pulses, the formation of shear bending waves with strong losses due to the lateral movement of the SWG's can also be prevented by the fact that, within the interaction length between the waves, no constructive reinforcement of the shear bending waves can take place. If $T_p$ is the pulse duration of the coupled-in sound waves, then the following is to apply preferably in this connection:

$$\frac{T_p^2 \cdot f_o}{D} > 2.5 \cdot 10^{-4} \text{ s/m}$$

This effect can be understood when assuming that the maximum interaction length between axial waves and shear bending waves is determined by the differential velocity between these waves multiplied by the pulse duration. The indicated relationship ensures that this interaction length is so short that no effective over-coupling of sonic energy takes place from axial waves to shear bending waves.

In SWG's for the transmission of short ultrasonic pulses, the difficulty occurs that the pulses are widened by the transmission. A dependency of the spectral sonic velocity (not detected by the group velocity but rather being of a "higher order") on the SWG geometry has been recognized as the cause therefor. This effect occurs, above all, for the torsional waves of a higher order; they are thus normally unsuitable for the transmission of short sonic pulses. However, in the single-wave SWG's according to this invention, as indicated above, the torsional fundamental wave is free of dispersion—therefore, they will present hardly any difficulties in the transmission of short sonic pulses.

In the axial waves of the SWG's according to the invention, a dispersion occurs that is only weak from the beginning; this dispersion can be further reduced
  (i) if the SWG geometry is maximally uniform (thus, SWG's of circular cross section are advantageous in this respect) or
  (ii) if the SWG consists of materials which differ as little as possible with regard to their mechanical properties (modulus of elasticity, shear modulus, Poisson ratio, and density), i.e. if the SWG is homogeneous.

For this reason, SWG's of a homogeneous material with a circular cross section are preferred for applications wherein it is important for the sonic pulses to show only minor widening.

However, these effects can also be avoided by maintaining the following conditions for the pulse duration $T_p$ of the sonic pulses, the SWG length L (transmission length between sonic transducers and directional elements), the SWG diameter D (maximum diameter in case of SWG's having a noncircular cross-sectional profile), and the carrier frequency $f_o$: for SWG's on Be basis $$\frac{T_p^2}{D^2 \cdot f_o \cdot L} \geq 3 \cdot 10^{-13} \text{ (s/m)}^3$$

for SWG's based on silica glass or made of W alloys $$\frac{T_p^2}{D^2 \cdot f_o \cdot L} \geq 6.7 \cdot 10^{-12} \text{ (s/m)}^3$$

and for SWG's of other materials $$\frac{T_p^2}{D^2 \cdot f_o \cdot L} \geq 2.1 \cdot 10^{-11} \text{ (s/m)}^3$$

(larger than-equal to relationship; the values on the right-hand side have the dimension of second$^3$ divided by meter$^3$). The fact that smaller values are permissible for Be, silica glass or tungsten SWG's can again be traced back to the low Poisson ratio.

When maintaining these values, it is ensured that the widening of the ultrasonic pulses by the transmission is markedly smaller than the duration of the ultrasonic pulses $T_p$. This will be enough for most of the cases arising under practical conditions. However, even higher demands could occur for applications with highest resolution. For example, it could be necessary for the widening of the sonic pulses to be short even in comparison with the duration of a vibration of the sound wave ($\approx 1/f_o$). In such a case, the previously indicated condition generally no longer suffices, and the following is to apply for SWG's on Be basis $$\frac{T_p^2}{D^2 \cdot f_o \cdot L} \geq 6 \cdot 10^{-13} \text{ (s/m)}^3$$

for SWG's based on silica glass or made of W alloys $$\frac{T_p^2}{D^2 \cdot f_o \cdot L} \geq 13 \cdot 10^{-12} \text{ (s/m)}^3$$

and for SWG's of other materials $$\frac{T_p^2}{D^2 \cdot f_o \cdot L} \geq 4 \cdot 10^{-11} \text{ (s/m)}^3$$

There is no need for any realistic case of application to maintain values that are still higher.

The SWG can optionally be surrounded by a fixedly mounted protective envelope of one or several layers. The protective envelope protects the SWG from chemical effects by the surrounding medium (e.g. atmosphere, body fluids or rinsing fluids) or avoids formation of scratches in the SWG surface, for example due to clumsy handling. When designed in accordance with this invention, the protective sheath has a negligible effect on the mechanical properties of the SWG's and on their capability of guiding sound waves.

The application of this protective envelope is recommended, in particular, with SWG's of glass because with these brittle materials even microscopic scoring on the SWG surface will considerably reduce the strength of the SWG's. The protective envelope can consist, for example, of a (ductile) synthetic resin, such as the UV-curable acrylates, silicones or polyimides utilized in fiber optics (in such a case, the SWG's could be sterilized at high temperatures), or of a thin metal layer.

In case of SWG's of metallic materials, there is usually no need for providing the protective sheath. However, if a protective envelope is to be applied, for example of gold for rendering the SWG's chemically inert, then it is recommended to utilize one of the many conventional electrolytic methods.

The SWG's of this invention made of glass can involve, in principle, the optical fibers known per se in optical communications technology. Designing the SWG's of this invention as optical fibers can have considerable advantages:

The optical fiber can, for example, transmit light energy serving for illumination of the sighted object in an ultrasonic probe designed as an endosonograph.

By the transmission of optical signals with the SWG, its condition in operation can be controlled, and any breakage can be detected rapidly and without disassembly of the probe.

When using an optical fiber as the SWG, it is preferred that this be a staggered-index fiber (core-clad fiber). In case of fibers based on silica glass, the core, in case of core-clad fibers, can consist of pure $SiO_2$ surrounded by an $SiO_2$ jacket that is weakly F-doped wherein the F doping effects the reduction in the index of refraction of the jacket with respect to the core, necessary for optical beam guidance. The F doping here is normally so minor that the mechanical properties of the $SiO_2$ glass are only slightly adversely affected.

However, with F doping, only a small difference in the refractive index between core and cladding of the fibers can be achieved. The resultant numerical aperture of the fibers can be too small under certain conditions for capturing sufficient radiation at the coupling-in end for an adequate illumination of the sighted object at the coupling-out end. In such a case, it is recommended that the fibers are produced as a core-clad SWG from multicomponent glasses. In this connection, care must be taken that during the drawing of these fibers no mechanical stresses are "frozen into" the fiber. These stresses can be caused, for example, by differing temperature expansion coefficients of the core glass and the cladding glass. Glass manufacturers know the types of glasses to be selected so that in the fibers drawn therefrom the mechanical stresses between core and cladding are small.

The SWG can have a cross section variable in the axial direction. In particular, the case is included that the cross section varies only at the coupling-in or coupling-out end for the sound waves and is essentially constant in the long central portion. The variation of the cross section can involve a flaring of the SWG ("taper") in order to simplify coupling of the sound waves into and, respectively, out of the SWG.

It is recommended that the diameter D (or the largest chord through the cross section in case of a noncircular cross section) of the flaring section of the SWG be smaller than the sonic wavelength of the axial waves ($\lambda = c_o/f_o$): $D > \lambda$. As a result, when passing the taper, the wave fronts of the sound waves which, in the SWG of this invention, are actually very planar are only slightly deformed in the SWG, i.e. in such a case the coupling of the axial waves to radial waves is there negligibly small.

The SWG according to this invention is to serve primarily for transmitting the sound waves from an ultrasonic transducer located at the proximal end of the probe to a directional element present at the distal end (beamed-in sonic signals). However, it can also serve for transporting the sound waves received by an ultrasonic receiver at the distal end to an electroacoustic transducer at the proximal end of the probe. Optionally, this transducer is identical to the transducer that produces the beamed-in signals. The ultrasonic receiver can be the ultrasonic directional element which also serves for transmitting the sonic pulses. For to and fro transmission, the same SWG can then be employed. The ultrasonic directional element for transmitting the sound waves and the ultrasonic receiver can, however, also be separate components. In this case, different SWG's are usually employed for the to and fro transmission of the sound waves.

The SWG can be subdivided along its extension so that it is possible to operate several ultrasonic directional elements with the ultrasonic transducer.

Several initially separate SWG's can be combined into a joint SWG so that it is possible to supply a directional head with several separate ultrasonic transducers (the SWG can, however, also be subdivided again and can lead to several transducers). This arrangement presents advantages if a transducer is to be supplied with several markedly separate sonic frequencies because the ultrasonic transducers, optimized in the usual sense, are tuned to a fixed frequency, or if a directional element is to be operated in multipulse operation with short pulses and a high repetition rate because the production of the sonic pulses is technically simpler with the separate sonic transducers.

For purposes of simplification, devices for medical uses (examinations of patients, tissue) have been described as a rule, although similar appliances can be utilized in technical applications (examination of articles, nondestructive material testing). The feature that the SWG's for transmission of sonic energy can also find use in technical areas is considered to be included in the invention.

The invention includes the aspect that the ultrasonic probes according to this invention are throughflow measuring devices, especially so-called intravascular or perivascular "flowmeters" for medical applications. Such flowmeters can operate according to the Doppler principle, the "transit time principle" (mono- and bidirectionally), or according to the "multi-element principle" (inhomogeneities entrained with the flow pass by several ultrasonic recording elements arranged in succession in the flow direction; from the chronological sequence of the recording pulses, the velocity of the flow is determined). In the conventional flowmeters, the ultrasonic transducers are located directly at the directional elements denoted as coupling-in sites (compare U.S. Pat. No. 4,257,275 for a flowmeter according to the multi-element principle, or U.S. Pat. No. 4,227,407 for a flowmeter according to the transit time principle), with the aforedescribed drawbacks. In the flowmeters according to this invention, the coupling-in sites are connected by way of SWG's with spatially separate transducers.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following example, all temperatures are set forth uncorrected in degrees Celsius; and, unless otherwise indicated, all parts and percentages are by weight.

The entire disclosure of all applications, patents and publications, cited above and below, and of corresponding German Application P 41 03 145, filed Feb. 2, 1991, are hereby incorporated by reference.

PRACTICAL EXAMPLE

For a sonograph for medical applications, operating according to the pulse echo method (transluminally guided probe for the intravascular determination of the plaque thickness of arteries, for example A. poplitea), sonic pulses are to be transmitted with an SWG according to this invention with a carrier frequency of $f_o=7.5$ MHz and a pulse duration of $T_p=533$ ns (wave trains with 4 cycles). In the biological tissue, the sonic pulse traverses about 80 μm within the pulse duration, thus corresponding approximately to the depth resolution capacity of the sonograph. This depth resolution capacity is adequate, according to the presently prevailing state of knowledge, for the intended use—furthermore, a higher resolution would require a higher carrier frequency, but then a substantially higher sound absorption would have to be expected (above all in calcified tissue). The repetition frequency of the sonic pulses amounts to 240 Hz. The peak power of the sonic pulses is 40 W and thus is relatively high (in spite of the low average output of about 0.5 mW). The necessary transmission length from the extracorporeal transducer to the probe head introduced into the body is 75 cm. The fiber is to be flexible with a radius of R=2 cm ("flexible SWG").

A simple embodiment is chosen, namely a fiber of pure silica glass having a circular cross section. The diameter of the fiber (of the glass body of the fiber, the mechanically active zone) is 62.5 μm. Consequently, many structural elements (plugs, lead-throughs, gaskets, etc.) can be utilized for the fiber, as employed in the communications technique for optical monomode fibers. For a transluminal probe, it is not necessary for the SWG to be designed as an optical fiber (although the use of optical fibers is obvious in connection with silica glass fibers); the SWG can consist of a homogeneous material. The SWG (the fiber) is, however, provided with a thin protective envelope of a UV-curable acrylate as customary in optical fibers.

Axial waves are coupled into the SWG. The product from the carrier frequency of the sound waves and the diameter of the fiber is 469 m/s. The wavelength for sound waves with the above-mentioned carrier frequency is 773 μm (in silica glass, the sonic velocity for axial waves is 5,800 m/s). The ratio of the fiber diameter and the sound wavelength is thus relatively low; a relatively strong dispersion is to be expected. The following is found for the governing "dispersion parameter" for the SWG according to this invention:

$$\frac{T_p^2}{D^2 \cdot f_o \cdot L} = 13 \cdot 10^{-12} \text{ (s/m)}^3$$

that is just the lower value of the range characterizing SWG's of low dispersion.

For the SWG, the product from the length and the square of the carrier frequency amounts to $L \cdot f_o^2 = 4.2 \cdot 10^{13}$ m/s²; the intrinsic sonic absorption of the silica glass is thus negligible.

The proposed SWG is of adequate mechanical flexibility to be introducible into a vacant endoscoping duct of a transluminal catheter. However, it is still sufficiently stiff for being able to enter without kinks; no supporting elements are required.

Coupling of the axial waves to shear bending waves is weak; the following is found for the parameter which represents the interaction length for constructive overcoupling of sonic energy between these waves:

$$\frac{T_p^2 \cdot f_o}{D} = 0.034 \text{ (s/m)}$$

Directional elements suitable for such an ultrasonic probe are disclosed, for example, in U.S. Pat. No. 4,508,122; suitable transducers based on a piezoceramic element are found, for example, in DOS 1,207,123.

The preceding example can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An ultrasonic probe having proximal and distal ends, comprising at least one ultrasonic directional element in the probe head at the distal end of the probe, at least one ultrasonic transducer located in the operating unit at the proximal end of the probe, and at least one ultrasonic waveguide means capable of transmitting ultrasonic waves in torsional or axial modes having a carrier frequency $f_0$ between 450 kHz and 28 MHz disposed between the ultrasonic transducer and ultrasonic directional element, wherein the sonic waveguide has a cross-section with a diameter ranging between 20 μm and 1000 μm and wherein the maximum value of the product $D \cdot f_0$ of the diameter D and the carrier frequency $f_0$ of the ultrasonic waves is less than 5100 m/s for torsional waves and less than 4200 m/s for axial waves in the waveguide.

2. An ultrasonic probe according to claim 1, wherein the ultrasonic waveguide is approximately circular in cross-section.

3. An ultrasonic probe according to claim 2, wherein the ultrasonic waveguide has a diameter smaller than 800 μm.

4. An ultrasonic probe according to claim 3, wherein the ultrasonic waveguide has a diameter ranging from between 60 μm and 600 μm.

5. An ultrasonic probe according to claim 1, wherein the ultrasonic waveguide is non-circular in cross-section with a minimum diameter $D_{min}$ and a maximum diameter $D_{max}$.

6. An ultrasonic probe according to claim 5, wherein the ratio $D_{max}/D_{min}$ of the maximum diameter $D_{max}$ to the minimum diameter $D_{min}$ is at least 1.4.

7. An ultrasonic probe according to claim 1, wherein the ultrasonic waveguide has a diameter smaller than 350 μm.

8. An ultrasonic probe according to claim 1, wherein the ultrasonic waveguide is made from a material selected from the group consisting of doped and undoped silica glass.

9. An ultrasonic probe according to claim 1, wherein the ultrasonic waveguide is an optical fiber, and the probe comprises means for coupling light into that fiber.

10. An ultrasonic probe according to claim 9, wherein the ultrasonic waveguide is an optical fiber being adapted to transmit ultrasonic waves and optical radiation.

11. An ultrasonic probe according to claim 10, wherein the optical fiber transmits ultrasonic waves and optical radiation simultaneously.

12. An ultrasonic probe according to claim 1, wherein the length of the ultrasonic waveguide ranges from between 8 cm and 5 m.

13. An ultrasonic probe according to claim 1, wherein the ultrasonic waveguide is made of glass, and wherein the condition $L \cdot f_0^2 \leq 8 \cdot 10^{13}$ m/s$^2$ applies for a transmission waveguide length L at the carrier frequency $F_0$.

14. An ultrasonic probe according to claim 1, wherein the ultrasonic waveguide is made of glass and wherein the condition $L \cdot f_0^2 \leq 8 \cdot 10^{11}$ m/s$^2$ applies for the transmission length L and the carrier frequency $f_0$.

15. An ultrasonic probe according to claim 1, wherein the ultrasonic waveguide is made of silica glass, and wherein the condition $L \cdot f_0^2 \leq 10^{16}$ m/s$^2$ applies for the transmission length L and the carrier frequency $f_0$.

16. An ultrasonic probe according to claim 1, wherein the ultrasonic waveguide is made of silica glass, and wherein the condition $L \cdot f_0^2 \leq 1 \cdot 10^{15}$ m/s$^2$ applies for the transmission length L and the carrier frequency $f_0$.

17. An ultrasonic probe according to claim 1 for the transmission of axial waves, wherein the ultrasonic waveguide is made of glass and wherein the condition $T_p^2/(D^2 \cdot f_0 \cdot L) \geq 2.1 \cdot 10^{-11}$ (s/m)$^3$ applies for the transmission length L, the carrier frequency $f_0$, the pulse duration $T_p$, and the diameter D of a ultrasonic waveguide with circular cross section, or, respectively, the minimum value of the chord through the cross-sectional surface in case of an ultrasonic waveguide having a non-circular cross-section.

18. An ultrasonic probe according to claim 1, wherein the transmission of axial waves, wherein the ultrasonic waveguide is made of silica glass and wherein the condition $T_p^2/(D^2 \cdot f_0 \cdot L) \geq 6.7 \cdot 10^{-12}$ (s/m)$^3$ applies for the transmission length L, the carrier frequency $f_0$, the pulse duration $T_p$, and the diameter D of an ultrasonic waveguide with circular cross-section, or, respectively, the minimum value of the chord through the cross-sectional surface in case of an ultrasonic waveguide having a non-circular cross-section.

19. An ultrasonic probe according to claim 1 for the transmission of axial waves, wherein the lateral movement of the ultrasonic waveguide is limited by supporting elements wherein, for the distance $L_{st}$ along the ultrasonic waveguide axis, the relationship $L_{st} \leq \sqrt{520 \text{ m/s}} \cdot D/f_0$ holds, wherein $f_0$ is the carrier frequency of the ultrasonic waves and D is the diameter of an ultrasonic waveguide with circular cross-section, or, respectively, the minimum value of the chord through the cross-sectional surface in case of an ultrasonic waveguide having a non-circular cross-section.

20. An ultrasonic probe according to claim 1, wherein the distance $L_{st}$ of the supporting elements along the ultrasonic waveguide axis the relationship $L_{st} \geq (3150 \text{ m/s})/f_0$ holds, wherein $f_0$ is the carrier frequency of the ultrasonic waves and D is the diameter of an ultrasonic waveguide with circular cross-section, or, respectively, the minimum value of the chord through the cross-sectional surface in case of an ultrasonic waveguide having a non-circular cross-section.

21. An ultrasonic probe according to claim 1 for the transmission of axial waves, wherein the condition $T_p^2 \cdot f_0/D \geq 2.5 \cdot 10^{-4}$ (s/m), applies for the carrier frequency $f_0$, the pulse duration $T_p$, and the diameter D of a ultrasonic waveguides with circular cross-section, or, respectively, the minimum value of the chord through the cross-sectional surface in case or an ultrasonic waveguide having a non-circular cross-section.

22. An ultrasonic probe according to claim 1, wherein the ultrasonic waveguide is disposed in a flexible or rigid probe tube.

* * * * *